US011559290B2

(12) United States Patent
Herdina et al.

(10) Patent No.: US 11,559,290 B2
(45) Date of Patent: *Jan. 24, 2023

(54) NAVIGABLE ENDOBRONCHIAL TOOL TO ACCESS TISSUE OUTSIDE A BRONCHUS

(71) Applicant: Covidien LP, Mansfield, MA (US)

(72) Inventors: Katherine A. Herdina, Vallejo, CA (US); Carol L. Shaffer, Plymouth, MN (US)

(73) Assignee: Covidien LP, Mansfield, MA (US)

( * ) Notice: Subject to any disclaimer, the term of this patent is extended or adjusted under 35 U.S.C. 154(b) by 364 days.

This patent is subject to a terminal disclaimer.

(21) Appl. No.: 16/784,448

(22) Filed: Feb. 7, 2020

(65) Prior Publication Data

US 2020/0170628 A1 Jun. 4, 2020

Related U.S. Application Data

(63) Continuation of application No. 15/399,984, filed on Jan. 6, 2017, now Pat. No. 10,582,914.
(Continued)

(51) Int. Cl.
*A61B 10/02* (2006.01)
*A61B 1/267* (2006.01)
(Continued)

(52) U.S. Cl.
CPC ............ *A61B 10/02* (2013.01); *A61B 1/2676* (2013.01); *A61B 5/06* (2013.01); *A61B 5/08* (2013.01);
(Continued)

(58) Field of Classification Search
CPC ....... A61B 10/02; A61B 34/20; A61B 1/2676; A61B 5/06; A61B 5/08; A61B 5/6852;
(Continued)

(56) References Cited

U.S. PATENT DOCUMENTS 3,598,108 A 8/1971 Jamshidi et al.
4,702,260 A 10/1987 Wang
(Continued)

FOREIGN PATENT DOCUMENTS

WO 0010456 A1 3/2000
WO 0167035 A1 9/2001
(Continued)

OTHER PUBLICATIONS

Extended European Search Report issued in Appl. No. EP 17151560.4 dated May 24, 2017.
(Continued)

*Primary Examiner* — Christopher A Flory
(74) *Attorney, Agent, or Firm* — Carter, DeLuca & Farrell LLP (57) ABSTRACT

Methods, systems, and devices for accessing tissue outside a bronchus and marking the location of a biopsy are provided. The method includes loading a navigation plan into a navigation system with the navigation plan including a CT volume generated from a plurality of CT images, inserting an extended working channel (EWC) including a location sensor into a patient's airways, registering a sensed location of the EWC with the CT volume of the navigation plan, and selecting a target in the navigation plan located outside the periphery of a patient's airways. The method further includes navigating the EWC and location sensor proximate the target, inserting a piercing catheter into the EWC, piercing through an airway wall to reach the target, storing a position of the location sensor in the navigation system as a biopsy location, and performing a biopsy at the stored biopsy location.

20 Claims, 8 Drawing Sheets

Related U.S. Application Data (60) Provisional application No. 62/279,373, filed on Jan. 15, 2016.

(51) Int. Cl.

| | | |
|---|---|---|
| *A61B 5/00* | (2006.01) | |
| *A61B 5/08* | (2006.01) | |
| *A61B 5/06* | (2006.01) | |
| *A61B 34/20* | (2016.01) | |
| *A61B 6/03* | (2006.01) | |
| *A61B 6/12* | (2006.01) | |
| *A61M 25/00* | (2006.01) | |
| *A61M 25/01* | (2006.01) | |
| *A61B 17/34* | (2006.01) | |
| *A61B 17/24* | (2006.01) | |

(52) U.S. Cl.
CPC ............ *A61B 5/6852* (2013.01); *A61B 6/032* (2013.01); *A61B 6/12* (2013.01); *A61B 34/20* (2016.02); *A61M 25/005* (2013.01); *A61M 25/0082* (2013.01); *A61M 25/0136* (2013.01); *A61B 17/3478* (2013.01); *A61B 2017/242* (2013.01); *A61B 2034/2065* (2016.02); *A61M 2210/1035* (2013.01)

(58) Field of Classification Search
CPC ... A61B 6/032; A61B 6/12; A61B 2034/2065; A61B 17/3478; A61B 2017/242; A61M 25/005; A61M 25/0082; A61M 25/0136; A61M 2210/1035
See application file for complete search history.

(56) References Cited

U.S. PATENT DOCUMENTS

| | | | |
|---|---|---|---|
| 5,205,830 | A | 4/1993 | Dassa et al. |
| 5,891,114 | A | 4/1999 | Chien et al. |
| 5,899,892 | A | 5/1999 | Mortier et al. |
| 5,951,495 | A | 9/1999 | Berg et al. |
| 5,951,539 | A | 9/1999 | Nita et al. |
| 5,971,975 | A | 10/1999 | Mills et al. |
| 6,036,677 | A | 3/2000 | Javier, Jr. et al. |
| 6,042,578 | A | 3/2000 | Dinh et al. |
| 6,045,547 | A | 4/2000 | Ren et al. |
| 6,045,734 | A | 4/2000 | Luther et al. |
| 6,093,177 | A | 7/2000 | Javier, Jr. et al. |
| 6,117,150 | A | 9/2000 | Pingleton |
| 6,165,163 | A | 12/2000 | Chien et al. |
| 6,171,295 | B1 | 1/2001 | Garabedian et al. |
| 6,188,355 | B1 | 2/2001 | Gilboa |
| 6,193,699 | B1 | 2/2001 | Matsumoto |
| 6,217,565 | B1 | 4/2001 | Cohen |
| 6,224,803 | B1 | 5/2001 | Tiernan |
| 6,319,244 | B2 | 11/2001 | Suresh et al. |
| 6,368,316 | B1 | 4/2002 | Jansen et al. |
| 6,398,791 | B1 | 6/2002 | Que et al. |
| 6,508,805 | B1 | 1/2003 | Garabedian et al. |
| 6,579,484 | B1 | 6/2003 | Tiernan et al. |
| 6,582,536 | B2 | 6/2003 | Shimada |
| 6,635,047 | B2 | 10/2003 | Forsberg |
| 6,740,277 | B2 | 5/2004 | Howell et al. |
| 6,866,660 | B2 | 3/2005 | Garabedian et al. |
| 6,890,321 | B2 | 5/2005 | Luther et al. |
| 7,104,979 | B2 | 9/2006 | Jansen et al. |
| 7,112,298 | B2 | 9/2006 | Kampa et al. |
| 7,306,585 | B2 | 12/2007 | Ross |
| 7,435,239 | B2 | 10/2008 | Yatabe et al. |
| 7,507,229 | B2 | 3/2009 | Hewitt et al. |
| 7,534,317 | B2 | 5/2009 | Brustad et al. |
| 7,597,830 | B2 | 10/2009 | Zhou |
| 7,615,043 | B2 | 11/2009 | Zhou |
| 7,704,245 | B2 | 4/2010 | Dittman et al. |
| 7,758,514 | B2 | 7/2010 | Grigoryants et al. |
| 7,968,038 | B2 | 6/2011 | Dittman et al. |
| 7,985,213 | B2 | 7/2011 | Parker |
| 8,206,373 | B2 | 6/2012 | Zhou |
| 8,231,551 | B2 | 7/2012 | Griffin et al. |
| 8,317,772 | B2 | 11/2012 | Jansen et al. |
| 8,323,432 | B2 | 12/2012 | Quint |
| 8,357,103 | B2 | 1/2013 | Mark et al. |
| 8,377,035 | B2 | 2/2013 | Zhou et al. |
| 8,517,955 | B2 | 8/2013 | Keast et al. |
| 8,747,359 | B2 | 6/2014 | Pakter et al. |
| 8,795,255 | B2 | 8/2014 | Jansen et al. |
| 8,932,258 | B2 | 1/2015 | Blanchard et al. |
| 8,939,960 | B2 | 1/2015 | Rosenman et al. |
| 8,998,852 | B2 | 4/2015 | Blanchard et al. |
| 9,095,683 | B2 | 8/2015 | Hall et al. |
| 9,205,223 | B2 | 12/2015 | Wilson et al. |
| 9,307,960 | B2 | 4/2016 | Keast et al. |
| 10,582,914 | B2 | 3/2020 | Herdina et al. |
| 2003/0009185 | A1 | 1/2003 | Jessen |
| 2003/0018344 | A1 | 1/2003 | Kaji |
| 2003/0114871 | A1 | 6/2003 | Turnbull |
| 2005/0090802 | A1 | 4/2005 | Connors et al. |
| 2006/0241342 | A1 | 10/2006 | Macaulay et al. |
| 2007/0276362 | A1 | 11/2007 | Rioux et al. |
| 2008/0125752 | A1 | 5/2008 | Gunderson et al. |
| 2009/0143643 | A1 | 6/2009 | Weitzner |
| 2009/0204060 | A1 | 8/2009 | Desinger |
| 2009/0306699 | A1 | 12/2009 | Kadykowski |
| 2010/0041949 | A1* | 2/2010 | Tolkowsky ...... A61B 17/12104 600/117 |
| 2010/0160862 | A1 | 6/2010 | Howat et al. |
| 2011/0238041 | A1 | 9/2011 | Lim et al. |
| 2012/0253376 | A1 | 10/2012 | Liu |
| 2013/0012940 | A1 | 1/2013 | Desinger |
| 2013/0331734 | A1 | 12/2013 | Keast |
| 2014/0005478 | A1 | 1/2014 | Kennedy, II et al. |
| 2014/0046174 | A1 | 2/2014 | Ladtkow et al. |
| 2014/0046175 | A1 | 2/2014 | Ladtkow et al. |
| 2014/0046176 | A1 | 2/2014 | Ladtkow et al. |
| 2014/0046211 | A1 | 2/2014 | Ladtkow et al. |
| 2014/0046315 | A1 | 2/2014 | Ladtkow et al. |
| 2014/0046316 | A1 | 2/2014 | Ladtkow |
| 2014/0270441 | A1 | 9/2014 | Baker |
| 2014/0276051 | A1 | 9/2014 | Hoffman |
| 2014/0281961 | A1 | 9/2014 | Baker |
| 2014/0282216 | A1 | 9/2014 | Baker |
| 2014/0330272 | A1 | 11/2014 | Klink |
| 2015/0005763 | A1 | 1/2015 | Klink |
| 2015/0005769 | A1 | 1/2015 | Klink |
| 2015/0141809 | A1 | 5/2015 | Costello et al. |
| 2015/0141869 | A1 | 5/2015 | Costello et al. |
| 2015/0182716 | A1 | 7/2015 | Wolf |
| 2015/0190126 | A1 | 7/2015 | Weitzner |
| 2015/0202437 | A1 | 7/2015 | Franke |
| 2015/0265257 | A1 | 9/2015 | Costello et al. |
| 2016/0000302 | A1 | 1/2016 | Brown et al. |
| 2016/0000303 | A1 | 1/2016 | Klein et al. |
| 2016/0000356 | A1 | 1/2016 | Brown et al. |
| 2016/0000517 | A1 | 1/2016 | Kehat et al. |
| 2016/0000520 | A1 | 1/2016 | Lachmanovich et al. |
| 2016/0005162 | A1 | 1/2016 | Markov et al. |
| 2016/0005163 | A1 | 1/2016 | Markov et al. |
| 2016/0005168 | A1 | 1/2016 | Merlet |
| 2016/0005193 | A1 | 1/2016 | Markov et al. |
| 2016/0005220 | A1 | 1/2016 | Weingarten et al. |
| 2016/0005224 | A1 | 1/2016 | Greenburg |
| 2016/0005236 | A1 | 1/2016 | Lachmanovich et al. |
| 2016/0192983 | A1 | 7/2016 | Klink |
| 2018/0214010 | A1* | 8/2018 | Alterovitz ............ G06T 19/003 |

FOREIGN PATENT DOCUMENTS

| | | |
|---|---|---|
| WO | 2010004570 A1 | 1/2010 |
| WO | 2011070844 A1 | 6/2011 |

(56) References Cited

FOREIGN PATENT DOCUMENTS

| WO | 2016006342 A1 | 1/2016 |
|----|---------------|--------|
| WO | 2016040128 A1 | 3/2016 |

OTHER PUBLICATIONS

Examination Report issued in corresponding Appl. No. EP 17151560.4 dated Apr. 26, 2019 (4 pages).

* cited by examiner

NAVIGABLE ENDOBRONCHIAL TOOL TO ACCESS TISSUE OUTSIDE A BRONCHUS

CROSS-REFERENCE TO RELATED APPLICATIONS

The present application is a continuation of U.S. patent application Ser. No. 15/399,984, filed on Jan. 6, 2017, which claims the benefit of and priority to U.S. Provisional Patent Application No. 62/279,373, filed on Jan. 15, 2016, the entire contents of each of which are incorporated by reference herein.

FIELD

The present disclosure relates to an endobronchial tool, and more particularly, to devices, systems, and methods for navigating an endobronchial tool to access tissue located outside a bronchus.

BACKGROUND

A common interventional procedure in the field of pulmonary medicine is bronchoscopy, in which a bronchoscope is inserted into the airways through the patient's nose or mouth. When treating malignancies of the lung, microwave ablation systems are often used in conjunction with an electromagnetic navigation (EMN) system. One such system is described in U.S. Pat. No. 6,188,355 and published PCT Application Nos. WO 00/10456 and WO 01/67035, the entire contents of which are hereby incorporated by reference. An EMN system typically includes a bronchoscope, a catheter assembly containing a location sensor at its steerable distal tip (e.g. locatable guide), an extended working channel that extends beyond the reach of the bronchoscope and becomes a pathway to the target site for subsequent diagnostic tools (e.g., biopsy tools, treatment catheters or laser, cryogenic, radio frequency, or microwave tissue treatment probes), and a computer system which provides the physician, or user, with navigational views of the lung. Once the bronchoscope is inserted into a patient's lungs, the locatable guide with the extended working channel is inserted into the bronchoscope. Using the navigation system and the steerable distal tip, the locatable guide and extended working channel is navigated to a target location. The locatable guide is then removed, leaving the extended working channel in place. Subsequent diagnostic tools can then be inserted into the extended working channel and directed to the target location.

However, in some cases, the target location or target tissue may be located outside the bronchial walls. In this situation, it is necessary to first insert the locatable guide through the extended working channel to guide the extended working channel towards the target tissue until the bronchial walls are reached. Once the locatable guide reaches the bronchial walls, the locatable guide must be removed from the extended working channel and a tool capable of piercing the bronchial walls is inserted into the extended working channel. The tool is used to pierce the airway wall and extend to the target lesion. The extended working channel is pushed over the tool and placed outside the airway wall. In order to confirm location of the extended working channel with respect to the lesion with the EMN system, the piercing tool is taken out of the extended working channel and the locatable guide is reinserted. Once the target tissue is reached, the locatable guide is removed and a biopsy tool or other instrument may be inserted through the extended working channel in order to act on the targeted tissue (e.g., perform a biopsy or ablation of the targeted tissue).

There is a need for a tool, or locatable guide, capable of penetrating the bronchus to access tissue located outside the bronchial walls while maintaining the ability to provide the physician with positional information on EMN, thereby minimizing the number of steps necessary to reach a target location.

SUMMARY

Provided in accordance with the present disclosure is a bronchial piercing catheter assembly used to navigate to target tissue in a patient under EMN guidance. The bronchial piercing catheter assembly includes a handle, a shaft, and a catheter tip. The shaft extends from the handle and includes a proximal end and a distal end, with the distal end configured to penetrate tissue. The catheter tip is located on the distal end of the shaft and is designed to penetrate tissue. The catheter tip further includes a base member defined along a central longitudinal axis of the bronchial piercing catheter, a trailing tip member adjacent to the base member, wherein the trailing tip member tapers relative to the base member, and a leading tip member adjacent to the trailing tip member, wherein the leading tip member further tapers to a distal end.

According to aspects of the disclosure the trailing tip member tapers at an angle greater than the leading tip member when measured from a central longitudinal axis of the bronchial piercing catheter. The catheter tip may be formed of titanium. The catheter tip has a thickness ranging from about 0.06 inches to about 0.09 inches. In embodiments, the shaft includes an inner layer and an outer layer, wherein the inner layer is made at least in part of a composite. The inner layer may include of a braided polymer composite and may have a thickness ranging from about 0.05 inches to about 0.07 inches. In another embodiment, the distal end further includes a locatable guide, wherein the locatable guide includes a location sensor in operative communication with a navigation system.

According to further aspects of the disclosure, a method for marking a biopsy location in a patient's airways is also disclosed. The method includes loading a navigation plan into a navigation system. The navigation plan includes a CT volume generated from a plurality of CT images. The method further includes inserting an extended working channel (EWC) into a patient's airways, the EWC including a bronchial piercing catheter assembly with location sensor in operative communication with the navigation system, registering a sensed location of the probe with the CT volume of the navigation plan, selecting a target within the periphery outside the airways in the navigation plan, navigating the EWC and location sensor proximate the target, inserting a piercing catheter into the probe and piercing the airway walls to reach the target, storing a position of the location sensor in the navigation system as a biopsy location, and performing a biopsy at the stored biopsy location.

According to aspects of the disclosure, the method may further include placing a virtual marker corresponding to the biopsy location in at least one of a 3D model of the patient's airways generated from the CT volume or a local view of the patient's airways generated from a slice of the CT volume. The method may also include removing a locatable guide from the EWC prior to inserting the piercing catheter. In another aspect, the method may further include locking the piercing catheter relative to the extended working channel. In embodiments, the method may include inserting the piercing catheter into a target. In another embodiment, the method further includes advancing the EWC over the piercing catheter to secure the EWC in the target. In yet another embodiment, the method may further include removing the piercing catheter from the EWC and inserting a biopsy tool through the EWC to the target to perform the biopsy.

According to aspects of the disclosure, the piercing catheter of the method disclosed may include a catheter tip. The catheter tip may include a base member defined along a central longitudinal axis of the probe, a trailing tip member adjacent to the base member, wherein the trailing tip member tapers relative to the base member, and a leading tip member adjacent to the trailing tip member, wherein the leading tip member further tapers to a distal end. According to aspects of the disclosure the trailing tip member tapers at an angle greater than the leading tip member when measured from a central longitudinal axis of the bronchial piercing catheter. The catheter tip may be formed of a titanium metal. The catheter tip has a thickness ranging from about 0.06 inches to about 0.09 inches.

DETAILED DESCRIPTION

The present disclosure is related to medical instruments, systems, and methods used to navigate to a specific target tissue location. In particular, an endobronchial tool consisting of a polymeric catheter shaft and a distal tip capable of penetrating the bronchus to access tissue located within the periphery outside the airway is disclosed. Located at the distal end of the shaft is an electromagnetic position and orientation sensor array allowing for a continuous depiction of the current position of the endobronchial tool in a generated three-dimensional (3D) model of the pathway.

Detailed embodiments of such devices, systems incorporating such devices, and methods using the same as described below. However, these detailed embodiments are merely examples of the disclosure, which may be embodied in various forms. Therefore, specific structural and functional details disclosed herein are not to be interpreted as limiting, but merely as a basis for the claims and as a representative basis for allowing one skilled in the art to variously employ the present disclosure in virtually any appropriately detailed structure. While the following embodiments are described in terms of bronchoscopy of a patient's airways, those skilled in the art will realize that the same or similar devices, systems, and methods may be used in other lumen networks, such as, for example, the vascular, lymphatic, and/or gastrointestinal networks as well.

Figure 1A:
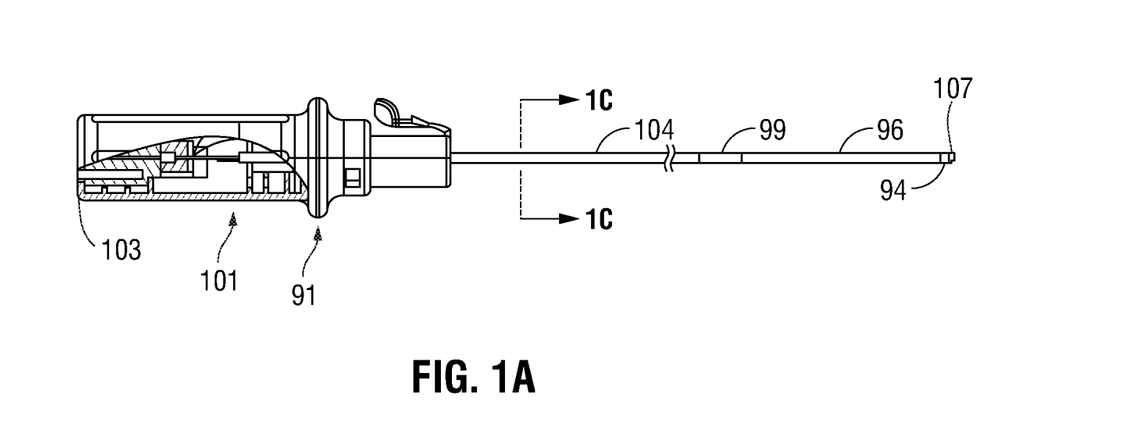
FIG. 1A is a profile view of a bronchial piercing catheter assembly in accordance with an embodiment of the present disclosure.

FIG. 1A is an exemplary embodiment of a bronchial piercing catheter 101 in accordance with one aspect of the present disclosure. The bronchial piercing catheter 101 includes a handle 91, a catheter shaft 104, and a distal piercing tip 107 with an EM sensor 94. The EM sensor 94 is similar to the EM sensor 94 described below with reference to FIG. 3. The catheter shaft 104 can be inserted in and navigated through extended working channel (EWC) 96. The catheter shaft 104 and EWC 96 are selectively lockable relative to one another via a locking mechanism 99.

Figure 1B:
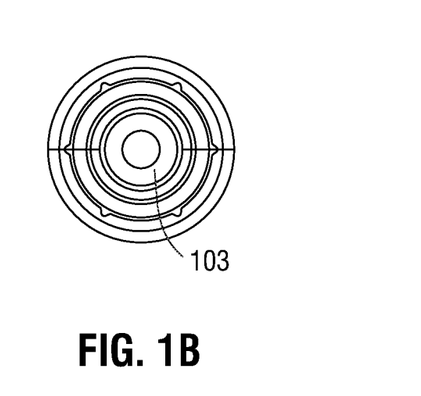
FIG. 1B is a side view of the proximal end of the bronchial piercing catheter assembly of FIG. 1A.
Figure 1C:
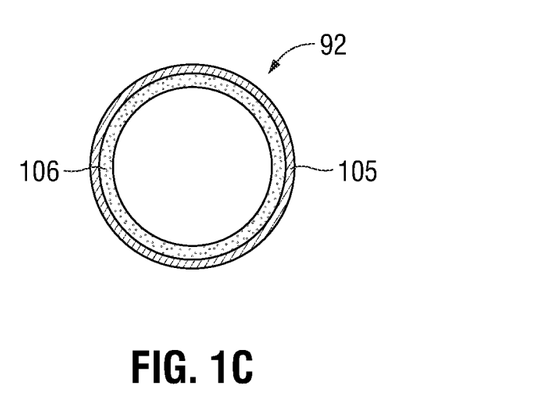
FIG. 1C is a cross-sectional view of the catheter shaft at the indicated area of FIG. 1A.

FIG. 1B shows a cross-sectional view of the proximal end of bronchial piercing catheter 101 containing an electrical connection 103 to allow the bronchial piercing catheter 101 to couple to a tracking system, as will be described in greater detail below. FIG. 1C depicts a cross-section of the catheter shaft 104. The catheter shaft 104 includes an outer polymer jacket 105 surrounding an inner layer 106 made from a braided polymer composite. The outer polymer jacket 105 has an outer diameter of 0.076 inches and may range from about 0.06 to about 0.09 inches, and has a thickness of about 0.008 inches. The inner layer 106 has an inner diameter of 0.060 inches and may range from about 0.05 to 0.07 inches.

Figure 2A:
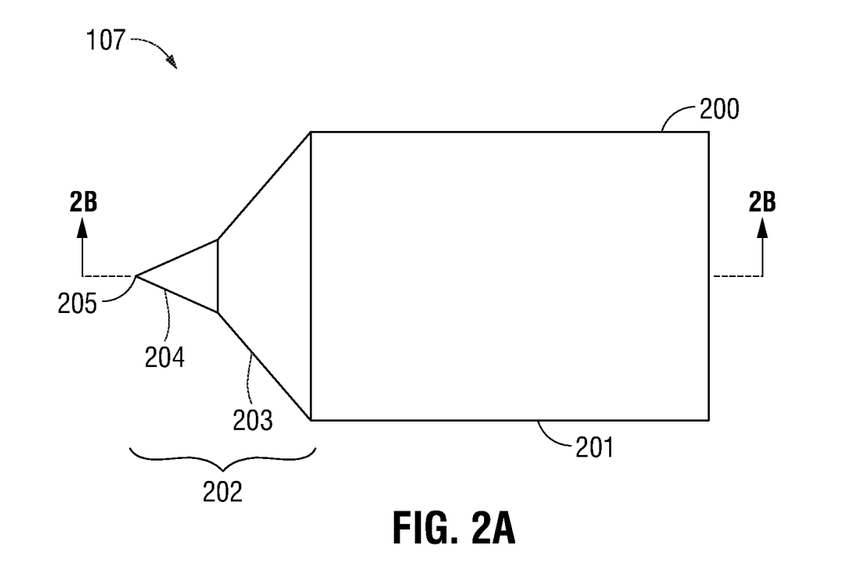
FIG. 2A is a profile view of the distal piercing tip of the bronchial piercing catheter assembly of FIG. 1A.
Figure 2B:
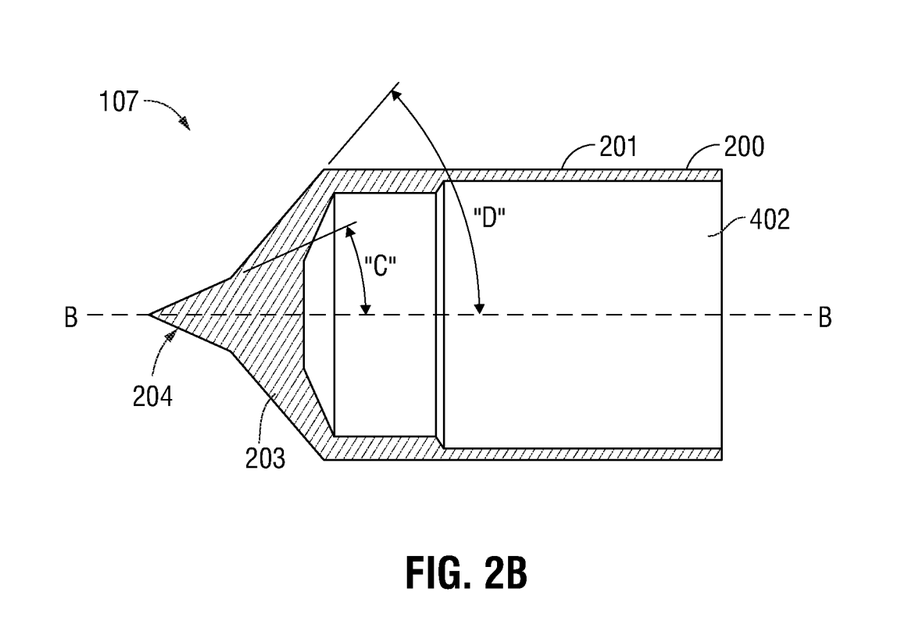
FIG. 2B is a cross-section view of the distal piercing tip depicted in FIG. 2A.

FIGS. 2A and 2B illustrate the distal piercing tip 107 of the bronchial piercing catheter 101 in accordance with one embodiment of the present disclosure. Distal piercing tip 107 includes a catheter tip 200 which is composed of two components, namely, a base member 201 defined along longitudinal axis "B" and a tip member 202. Tip member 202 of distal piercing tip 107 generally tapers inwardly towards the longitudinal axis "B" to penetrating end 205. Tip member 202 defines a leading tip section 204 adjacent penetrating end 205 and a trailing tip section 203. The diameter of leading tip section 204 gradually increases from penetrating end 205 to the area of intersection of leading tip section 204 and trailing tip section 203, in embodiments in a linear manner. Likewise, the diameter of trailing tip section 203 gradually increases from the leading tip section 204 to the base member 201. Thus, trailing tip section 203 tapers from the base member 201 to the leading tip section 204, and the leading tip section tapers further, in embodiments at a different angle, or pitch, than the trailing tip section 203, from the trailing tip section 203 to the penetrating end 205. Penetrating end 205 has a pointed tip that may have a sharpened edge to pierce tissue.

FIG. 2B depicts a cross-section of the distal piercing tip 107. As depicted in FIG. 2B, the catheter tip 200 is formed of a base member 201, a trailing tip section 203, and leading tip section 204. The catheter tip 200 may be formed of steel, aluminum, titanium or other appropriate metals. In embodiments, the base member 201 and the tip member 202 of the catheter tip 200 are machined from a single metal component. Alternatively, the catheter tip 200 may be formed of ceramic, a matrix material such as epoxies, or other materials suitable for the purposes described herein. As may be appreciated by one of ordinary skill in the art, various dimensions and angles may be used to fabricate the catheter tip 200. For example, in one embodiment, the catheter tip 200 may extend a length of about 0.165 inches over the distal piercing tip 107 and may range from about 0.1 to 0.2 inches. The leading tip section 204 may be about 0.023 inches in length and may range from about 0.02 to 0.04 inches. As measured from the central longitudinal axis "B" of the distal piercing tip 107, leading tip section 204 has an angle "C" of about 25 degrees and may range from about 20 to 30 degrees. The trailing tip section 203 may be about 0.027 inches in length and may range from about 0.02 to 0.04 inches. The trailing tip section 203 has an angle "D" of about 50 degrees and may range from about 45 to 55 degrees. The outer diameter of catheter tip 200 may be about 0.084 inches and may range from about 0.07 to 0.1 inches.

The change in angle from the leading tip section 204 to the trailing tip section 203 and from the trailing tip section 203 to the base member 201 helps limit unintentional piercing of tissue. Further because of the relatively short length of the leading tip section 204, the extent of such a piercing, should it occur, is also limited. As the bronchial piercing catheter 101 is navigated to the target tissue, the leading tip section 204 and penetrating end 205 may unintentionally prick or cut tissue, however, the increased angle of trailing tip section 203 ensures that the leading tip section 204 of the bronchial piercing catheter 101 does not completely pierce through the tissue unless extra force is exerted on the bronchial piercing catheter 101 by the clinician. In other words, for the distal piercing tip 107 to pierce through tissue beyond the trailing tip section 203, additional force must be applied.

Relatedly, the increased angle of the trailing tip section 203 acts as a blunt tipped dissector providing an angled surface which helps to increase the size of an opening created by the leading tip section 204 to at least the diameter of the base member 201 as the bronchial piercing catheter 101 is advanced through for example bronchial wall tissue, or other tissue between an opening in the bronchial wall and an intended target. As described below, an extended working channel (EWC) 96 (FIG. 3), within which the bronchial piercing catheter 101 is inserted, can then be advanced into the opening initially created by the leading tip section 204 and expanded by the trailing tip section 203. Such an arrangement eliminates the need for a second catheter or tissue expander as has been used previously, thus eliminating the need for another tool within the system, and the number of movements of tools required to advance a catheter to a desired target.

Figure 3:
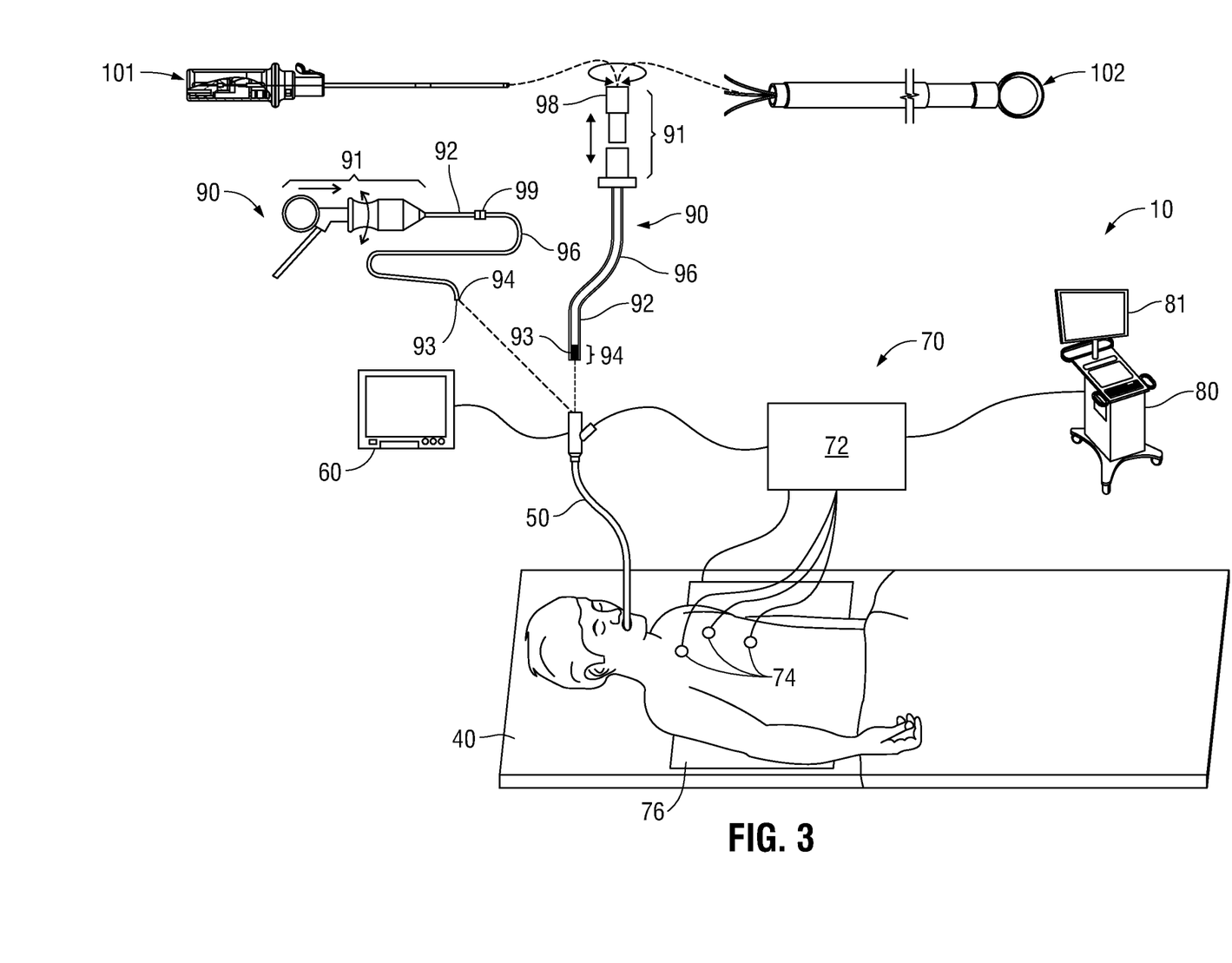
FIG. 3 is a perspective view of a system for identifying a location of a medical instrument in accordance with an embodiment of the present disclosure.

With reference to FIG. 3, an electromagnetic navigation (EMN) system 10 is provided in accordance with the present disclosure. One such EMN system is the ELECTROMAGNETIC NAVIGATION BRONCHOSCOPY® system currently sold by Medtronic, Inc. Among other tasks that may be performed using the EMN system 10 are planning a pathway to target tissue, navigating a positioning assembly to the target tissue, navigating a biopsy tool to the target tissue to obtain a tissue sample from the target tissue using the biopsy tool digitally marking the location where the tissue sample was obtained, and placing one or more echogenic markers at or around the target.

EMN system 10 generally includes an operating table 40 configured to support a patient, a bronchoscope 50 configured for insertion through the patient's mouth and/or nose into the patient's airways, monitoring equipment 60 coupled to bronchoscope 50 for displaying video images received from bronchoscope 50, a tracking system 70 including a tracking module 72, a plurality of reference sensors 74, an electromagnetic field generator 76, and a workstation 80 including software and/or hardware used to facilitate pathway planning, identification of target tissue, navigation to target tissue, and digitally marking the biopsy location.

FIG. 3 also depicts two types of catheter guide assemblies 90, 100. Both catheter guide assemblies 90, 100 are usable with the EMN system 10 and share a number of common components. Each bronchial piercing catheter assembly 90, 100 includes a handle 91, which is connected to an EWC 96. The EWC 96 is sized for placement into the working channel of a bronchoscope 50. In operation, a locatable guide (LG) 92, including an electromagnetic (EM) sensor 94, is inserted into the EWC 96 and locked into position such that the sensor 94 extends a desired distance beyond the distal tip of the EWC 96. The location of the EM sensor 94, and thus the distal end of the EWC 96, within an electromagnetic field generated by the electromagnetic field generator 76 can be derived by the tracking module 72, and the workstation 80. Catheter guide assemblies 90, 100 have different operating mechanisms. In one embodiment, catheter guide assemblies 90, 100 contain a handle 91 that can be manipulated by rotation and compression to steer the distal tip 93 of the LG 92, extended working channel 96. Catheter guide assemblies 90 are currently marketed and sold by Medtronic, Inc. under the name SUPERDIMENSION® Procedure Kits. Similarly catheter guide assemblies 100 are currently sold by Medtronic, Inc. under the name EDGE Procedure Kits. Both kits include a handle 91, extended working channel 96, and locatable guide 92. For a more detailed description of the catheter guide assemblies 90, 100 reference is made to commonly-owned U.S. Patent Application Publication No. 2014/0046315 filed on Mar. 15, 2013 by Ladtkow et al., the entire contents of which are hereby incorporated by reference.

As illustrated in FIG. 3, the patient is shown lying on an operating table 40 with a bronchoscope 50 inserted through the patient's mouth and into the patient's airways. Bronchoscope 50 includes a source of illumination and a video imaging system (not explicitly shown) and is coupled to monitoring equipment 60, e.g., a video display, for displaying the video images received from the video imaging system of bronchoscope 50.

Catheter guide assemblies 90, 100 including LG 92 and EWC 96 are configured for insertion through a working channel of bronchoscope 50 into the patient's airways (although the catheter guide assemblies 90, 100 may alternatively be used without bronchoscope 50). The LG 92 and EWC 96 are selectively lockable relative to one another via a locking mechanism 99. A six degrees-of-freedom electromagnetic tracking system 70, e.g., similar to those disclosed in U.S. Pat. No. 6,188,355 and published PCT Application Nos. WO 00/10456 and WO 01/67035, the entire contents of each of which is incorporated herein by reference, or any other suitable positioning measuring system is utilized for performing navigation, although other configurations are also contemplated. Tracking system 70 is configured for use with catheter guide assemblies 90, 100 to track the position of the EM sensor 94 as it moves in conjunction with the EWC 96 through the airways of the patient, as detailed below.

As shown in FIG. 3, electromagnetic field generator 76 is positioned beneath the patient. Electromagnetic field generator 76 and the plurality of reference sensors 74 are interconnected with tracking module 72, which derives the location of each reference sensor 74 in six degrees of freedom. One or more of reference sensors 74 are attached to the chest of the patient. The six degrees of freedom coordinates of reference sensors 74 are sent to workstation 80, which includes application 81 where sensors 74 are used to calculate a patient coordinate frame of reference.

In practice, the clinician uses the catheter guide assemblies 90, 100 to navigate the EWC 96 using the LG 92 to reach a desired exit location from within the luminal network of the lungs (e.g. the airways). Once the exit location is reached, the LG 92 is removed and the bronchial piercing catheter 101 is inserted into the EWC 96. The bronchial piercing catheter 101 is then advanced forward to pierce the bronchial walls while tracking its proximity to the target. Once placed in proximity to the target, the EWC 96 is also advanced forward. The bronchial piercing catheter 101 can then be removed, and a biopsy tool 102 can be inserted into the EWC 96 and advanced to the target. The use of the bronchial piercing catheter 101 allows the navigation of the EWC 96 to a target outside the airways and limits the need for live fluoroscopic images, thus reducing radiation exposure. In an alternative embodiment (not shown), the LG 92 is integrated with the bronchial piercing catheter 101. In this embodiment, the bronchial piercing catheter 101 is locked inside the EWC 96 so the distal end of the bronchial piercing catheter 101 is positioned inside the distal end of the EWC 96. The bronchial piercing catheter 101 (with the integrated LG 92) is then navigated with the EWC 96 to a desired exit location within the luminal network of the lungs. Once the exit location is reached, the bronchial piercing catheter 101 is advanced forward and locked relative to the EWC 96 in a second position in which the distal end of the bronchial piercing catheter 101 is just beyond the distal end of the EWC 96. The bronchial piercing catheter 101 and the EWC 96 are then advanced forward to pierce the bronchial walls while tracking its proximity to the target. This embodiment eliminates the step of removing the LG 92 in order to place the bronchial piercing catheter 101 through the EWC 96.

Of course, those of skill in the art will recognize that a blunt tipped dissector, or other tissue expander, including inflatable tissue expanders could be utilized in combination with the EWC 96 and the bronchial piercing catheter 101, without departing from the scope of the present disclosure. Other advantages of this embodiment, and the use of the trailing tip section 203 as a dissector, will be described in greater detail below.

Also shown in FIG. 3 is a biopsy tool 102 that is insertable into the catheter guide assemblies 90, 100 following navigation to a target and removal of the LG 92. The biopsy tool 102 is used to collect one or more tissue sample from the target tissue. The biopsy tool 102 may further be configured for use in conjunction with tracking system 70 to facilitate navigation of biopsy tool 102 to the target tissue, tracking of a location of biopsy tool 102 as it is manipulated relative to the target tissue to obtain the tissue sample, and/or marking the location where the tissue sample was obtained. During navigation, EM sensor 94, in conjunction with tracking system 70, enables tracking of EM sensor 94 and/or biopsy tool 102 as EM sensor 94 or biopsy tool 102 is advanced through the patient's airways.

A variety of useable biopsy tools are described in U.S. Patent Publication Nos. 2015/0141869 and 2015/0141809 both entitled DEVICES, SYSTEMS, AND METHODS FOR NAVIGATING A BIOPSY TOOL TO A TARGET LOCATION AND OBTAINING A TISSUE SAMPLE USING THE SAME, filed Sep. 17, 2014 and U.S. Patent Publication No. 2015/0265257 having the same title and filed Dec. 9, 2014, both by Costello et al., the entire contents of each of which are incorporated herein by reference and useable with the EMN system 10 as described herein.

In an alternative embodiment, a microwave ablation catheter can be inserted into the EWC 96 instead of a biopsy tool 102. In this embodiment, the bronchial piercing catheter 101 can be inserted into a desired location in the target tissue (e.g. a tumor or mass), and then the EWC 96 is advanced over the top of the bronchial piercing catheter 101 to secure the EWC 96 in the target tissue. This assures the microwave catheter reaches the target tissue. The bronchial piercing catheter 101 is then removed and the microwave catheter can be navigated to the target tissue through the EWC 96. In some embodiments the EWC 96 may have to be retracted after placement of the microwave ablation catheter to enable operation of the ablation catheter.

During procedure planning, workstation 80 utilizes computed tomographic (CT) image data for generating and viewing a three-dimensional model ("3D model") of the patient's airways, enables the identification of target tissue on the 3D model (automatically, semi-automatically or manually), and allows for the selection of a pathway through the patient's airways to the target tissue. More specifically, the CT scans are processed and assembled into a 3D volume, which is then utilized to generate the 3D model of the patient's airways. The 3D model may be presented on a display monitor 81 associated with workstation 80, or in any other suitable fashion. Using workstation 80, various slices of the 3D volume and views of the 3D model may be presented and/or may be manipulated by a clinician to facilitate identification of a target and selection of a suitable pathway through the patient's airways to access the target. The 3D model may also show marks of the locations where previous biopsies were performed, including the dates, times, and other identifying information regarding the tissue samples obtained. These marks may also be selected as targets to which a pathway can be planned. Once selected, the pathway is saved for use during the navigation procedure. An example of a suitable pathway planning system and method is described in U.S. Patent Publication Nos. 2014/0281961; 2014/0270441; and 2014/0282216, all entitled PATHWAY PLANNING SYSTEM AND METHOD, filed on Mar. 15, 2014, the entire contents of each of which are incorporated herein by reference.

Figure 4:
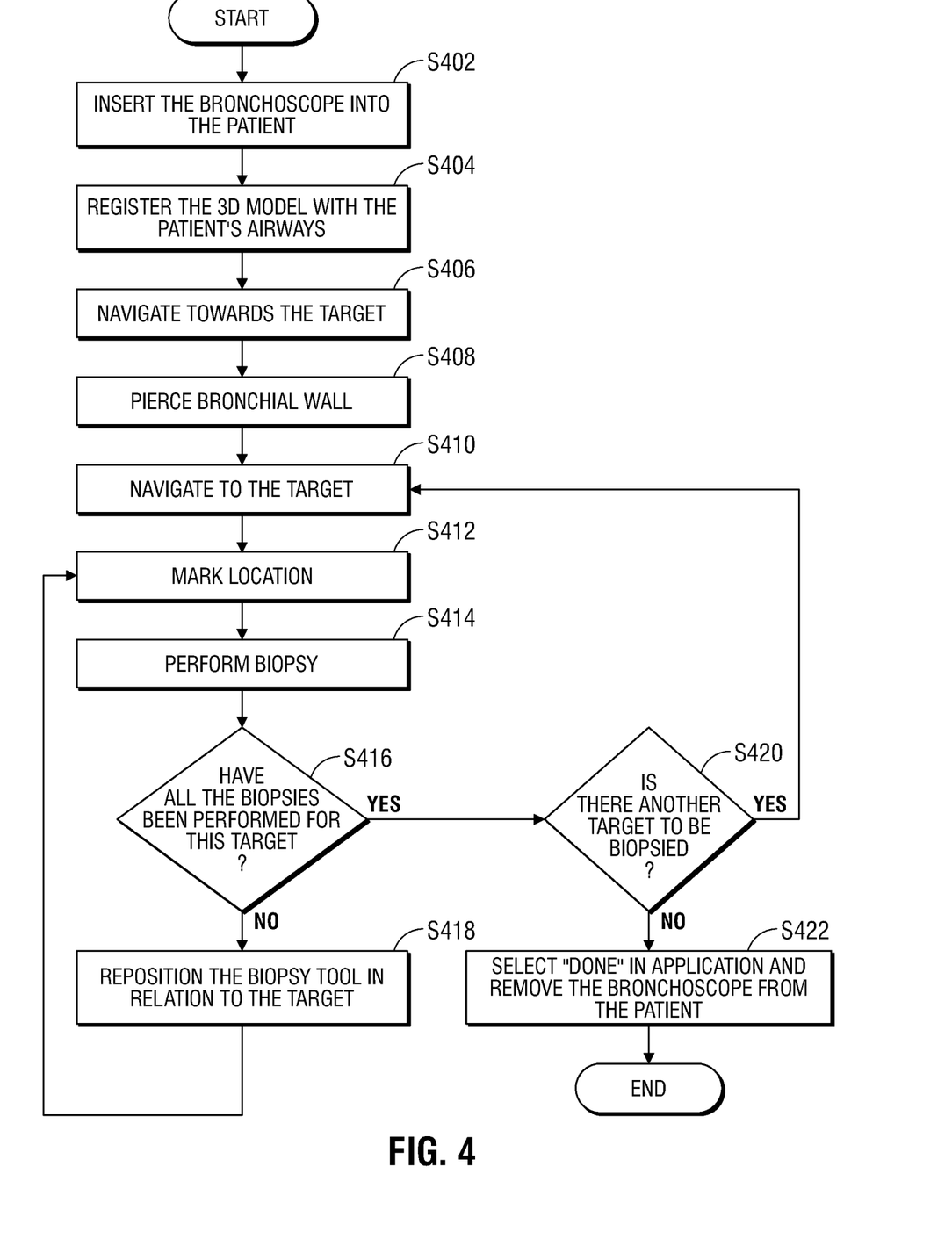
FIG. 4 is a flowchart of a method for navigating a bronchial piercing catheter through a patient's airways in accordance with an embodiment of the present disclosure.

FIG. 4 depicts a flowchart of an example method for navigating the bronchial piercing catheter 101 to a target tissue. Prior to the start of navigation, the clinician loads a navigation plan into application 81 from memory 802, a USB device, or from network interface 208. Initially, LG 92 and EWC 96 are locked together via locking mechanism 99 and inserted into bronchoscope 50 such that EM sensor 94 with distal tip 93 projects from the distal end of bronchoscope 50. The clinician then inserts bronchoscope 50 into the patient in step S402. Bronchoscope 50 may, for example, be inserted via the patient's mouth or nose.

The clinician advances bronchoscope 50, LG 92, and EWC 96 into each region of the patient's airways in step S404 until registration has occurred between the location of EM sensor 94 of LG 92 and the 3D volume of the navigation plan. Further disclosure of the process of registration is disclosed in U.S. patent application Ser. No. 14/790,581, entitled REAL-TIME AUTOMATIC REGISTRATION FEEDBACK, filed on Jul. 2, 2015, by Brown, the entire contents of which are incorporated herein by reference.

Figure 5:
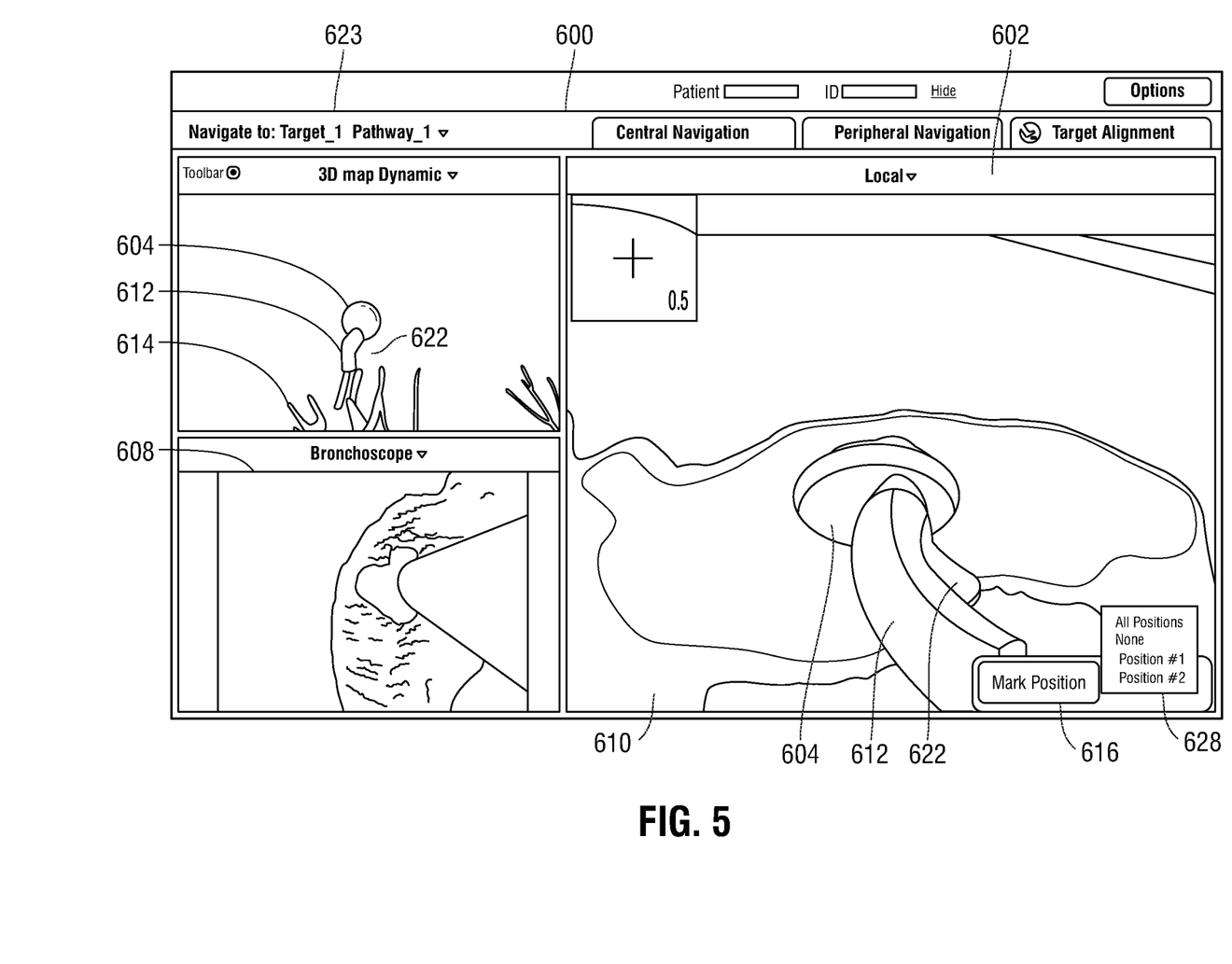
FIG. 5 is an illustration of a user interface of the workstation of FIG. 3 presenting a view for marking a biopsy location in accordance with the present disclosure.

Once registration is complete, user interface 816 presents the clinician with a view 600, similar to that shown in FIG. 5 to assist the clinician in navigating LG 92 and EWC 96 to the target 604. View 600 may include a local view 602, a 3D map dynamic view 606, and a bronchoscope view 608. Local view 602 presents the clinician with a slice 610 of the 3D volume located at and aligned with the distal tip 93 of LG 92. The slice 610 is presented from an elevated perspective. Local view 602 also presents the clinician with a visualization of the distal tip 93 of LG 92 in the form of a virtual probe 612. Virtual probe 612 provides the clinician with an indication of the direction that distal tip 93 of LG 92 is facing so that the clinician can control the advancement of the LG 92 and EWC 96 in the patient's airways.

3D map dynamic view 606 presents a dynamic 3D model 614 of the patient's airways generated from the 3D volume of the loaded navigation plan. The orientation of dynamic 3D model 614 automatically updates based on movement of the EM sensor 94 within the patient's airways to provide the clinician with a view of the dynamic 3D model 614 that is relatively unobstructed by airway branches that are not on the pathway to the target 604. 3D map dynamic view 606 also presents the virtual probe 612 to the clinician as described above where the virtual probe 612 rotates and moves through the airways presented in the dynamic 3D model 606 as the clinician advances the EM sensor 94 through corresponding patient airways.

Bronchoscope view 608 presents the clinician with a real-time image received from the bronchoscope 50 and allows the clinician to visually observe the patient's airways in real-time as bronchoscope 50 is navigated through the patient's airways toward target 604.

The clinician navigates bronchoscope 50 toward the target 604 until the patient's airways become too small for bronchoscope 50 to pass and wedges bronchoscope 50 in place. LG 92 and EWC 96 are then extended from bronchoscope 50 and the clinician navigates LG 92 and EWC 96 toward the target 604 using view 600 of user interface 816 in S406 until a barrier or bronchial walls are reached, preventing navigation of the LG 92 and EWC 96 towards the target 604. The LG 92 is then removed and the bronchial piercing catheter 101 is inserted into the EWC 96. In an alternative embodiment, the bronchial piercing catheter 101 is advanced through the airways without the need for the use of an LG 92 because the bronchial piercing catheter 101 may also be equipped with an EM sensor 94. The EM sensor on the piercing catheter 101 may operate alone or in combination with one or more EM sensors on the EWC 96. The clinician then applies additional force on the bronchial piercing catheter 101 to pierce through the barrier or bronchial walls in S408. The leading tip section 204 allows the bronchial piercing catheter 101 to pierce through the barrier and allow the EWC 96 to navigate further towards the target 604. The bronchial piercing catheter 101 is then advanced towards the target and the EWC 96 subsequently advanced over the bronchial piercing catheter 101 in S410 until the virtual probe 612 is adjacent to or inserted into target 604, as shown, for example, in FIG. 5.

Figure 6:
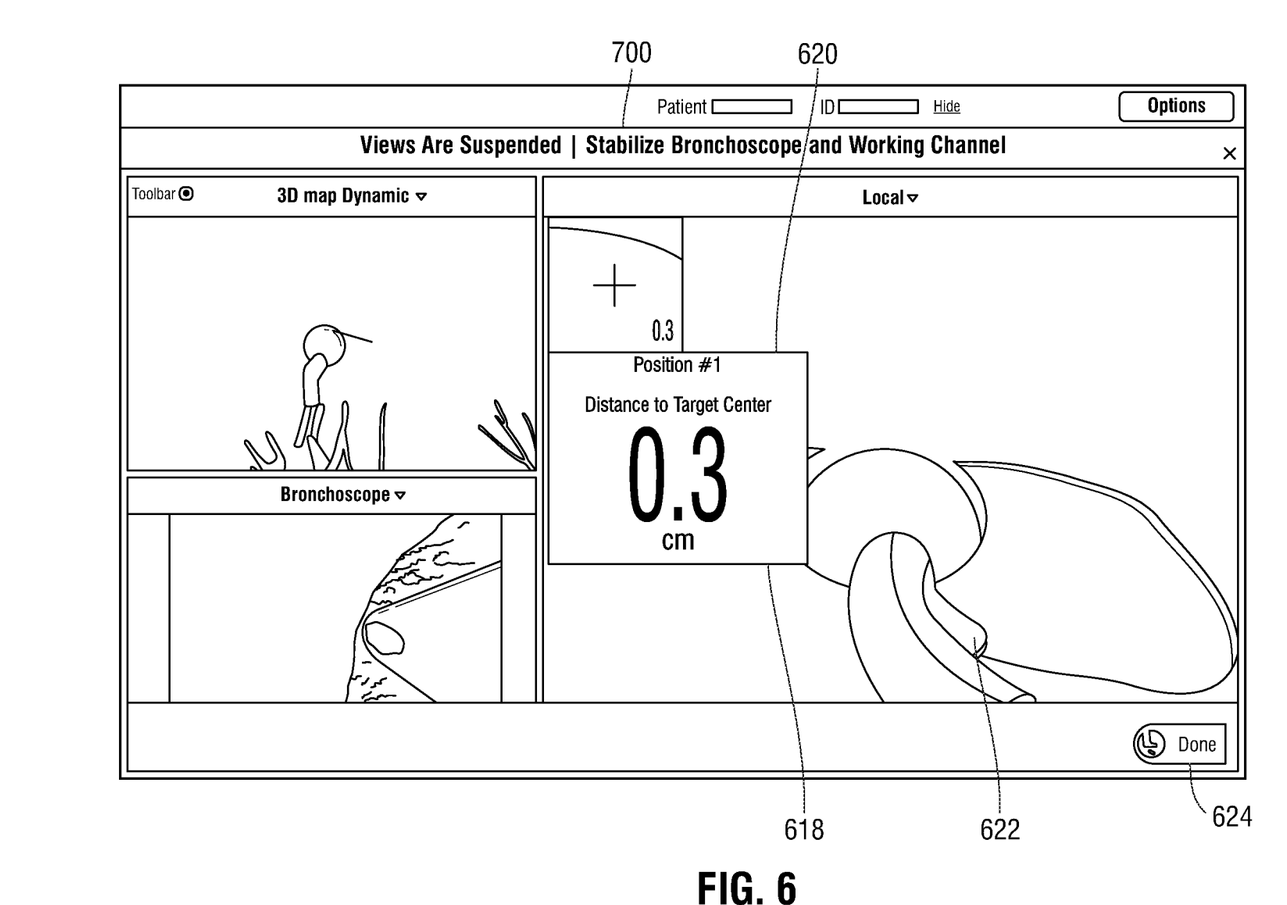
FIG. 6 is an illustration of the user interface of the workstation of FIG. 3 presenting a view for marking a location of a biopsy or treatment of the target.

The clinician may electronically mark the location of a biopsy by activating a "mark position" button 616 to virtually mark the position of virtual probe 612 in the 3D volume which corresponds to the registered position of EM sensor 94 on the piercing bronchial catheter 101 in step S412. Activating the "mark position" button 616 causes user interface 816 to present a view 700 including details of the marked position, as shown in FIG. 6. For example, view 700 may indicate a distance to the target center 618 and a biopsy position number 620. As described in greater detail below, this marked location of the biopsy is then stored in memory of the workstation 80 and associated with the record of the biopsy procedure for the patient. For example screen shots of the locations may be incorporated into a report for a clinician to consider when evaluating either the sufficiency of the biopsy or the adequacy of the sampling locations, etc. These reports and the data associated with them may also be stored as part of the patient's electronic medical record as would be understood by those of ordinary skill in the art.

After activating the "mark position" button 616, the clinician may remove piercing bronchial catheter 101 from EWC 96 and bronchoscope 50 and insert a biopsy tool 102 into bronchoscope 50 and EWC 96 to obtain a tissue sample at the target 604 in step S414. In some embodiments, the clinician then removes biopsy tool 102 from EWC 96 and bronchoscope 50 and reinserts LG 92. When LG 92 reaches the distal end of EWC 96, the clinician activates a "done" button 624 in view 700 indicating that the biopsy is complete. The EWC and LG 92 may then be utilized to navigate to another portion of that target or to another target, and the same steps as described above may be repeated until all targets are biopsied. Though described herein in a specific order, the perform biopsy step S414 and the mark location step S412 may be performed in any order.

During the biopsy, application 81 stores the position marked by virtual probe 612 within the patient's airways and places a virtual marker 622 in both the 3D model 614 and local view 602 of view 600 to mark the location where the tissue sample was obtained. The storing of the position and placement of virtual marker 622 may be performed upon activation of the "mark position" button 616 in view 600, during the biopsy, or upon activation of the "done" button 624 in view 700. Additionally, the location where the tissue sample is obtained may also be physically marked by, for example, implanting an echogenic marker or a dye which can be detected in future CT scans of the patient and in some instances compared to the locations of the virtual markers 622 stored in the CT image data and/or the navigation plan. In one embodiment, a marker is inserted in to the EWC 96 and advanced or pushed out of the EWC 96 using the LG 92 to mark the location the biopsy was taken. After the tissue sample is obtained and the location is marked, the clinician may remove biopsy tool 102 from bronchoscope 50 and provide the tissue sample to a rapid on-site evaluation ("ROSE") clinician for immediate testing or submit to a lab for routine testing.

The clinician determines in step S416 whether another biopsy needs to be performed at target 604. If another biopsy needs to be performed, the clinician repositions either LG 92 or bronchial piercing catheter 101 relative to target 604 in step S418 using view 600 and repeats steps S412 to S416. As described above, the use of bronchial piercing catheter 101 enables insertion of the EWC 92 into the target 604, thus holding it in the desired location while the bronchial piercing catheter 101 is removed and the biopsy tool is inserted. If no further biopsies are required for target 604, the clinician determines if there is another target to be biopsied in step S420. For example, the clinician may activate a target selection button 623 of view 600 to see if navigation to another target has been planned. If another target is available, the clinician may initiate navigation to the new target by activating target selection button 623 and may repeat steps S410 to S420 for the new target as described above.

Figure 7:
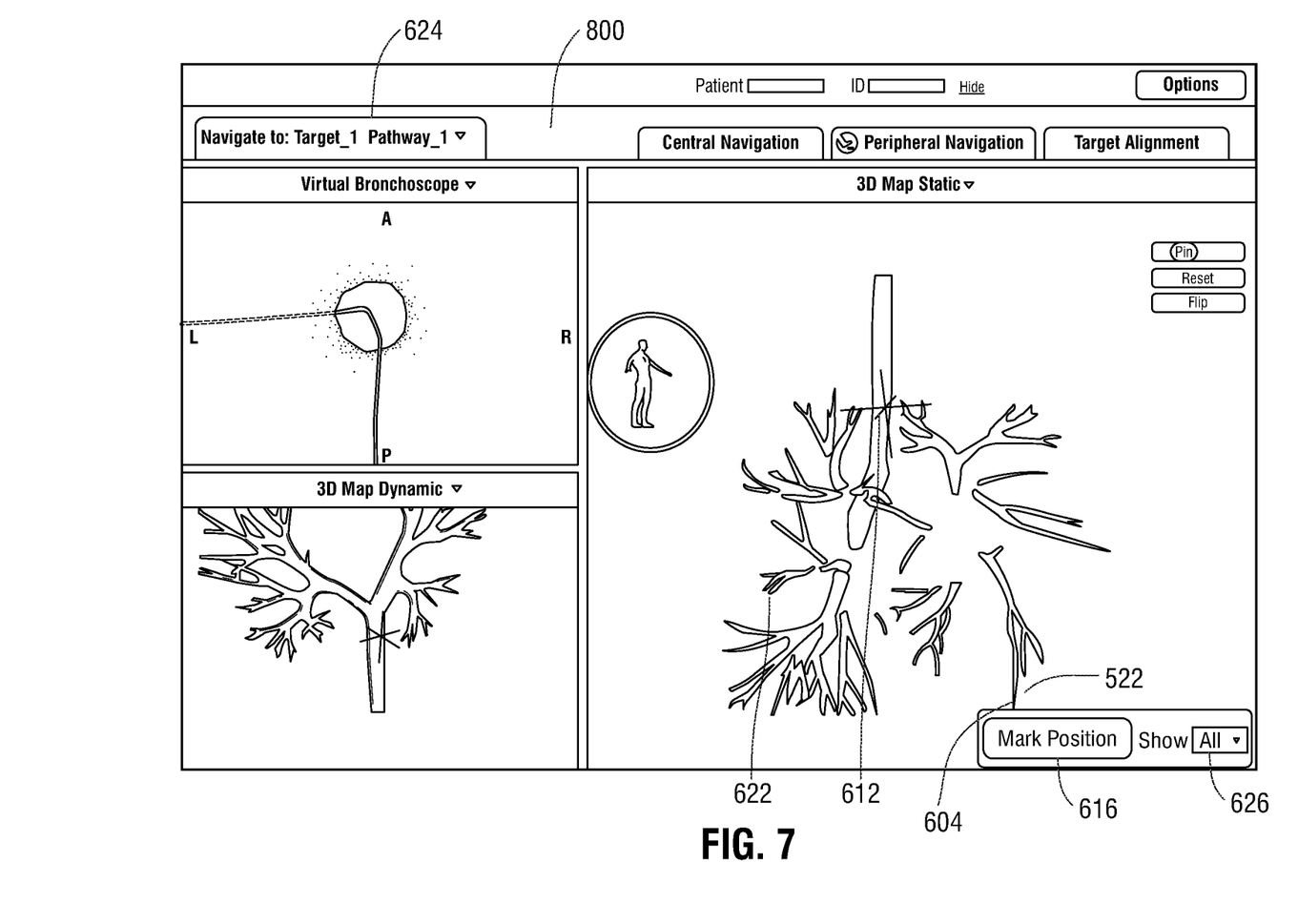
FIG. 7 is an illustration of the user interface of the workstation of FIG. 3 presenting a view showing multiple marked biopsy locations.

As illustrated in FIG. 7, a virtual marker 622 may be presented in view 800 for each marked biopsy location and the clinician may return to a specified biopsy location at a later time, for example, upon receiving a result of the ROSE testing to perform further biopsies or treatment. The virtual marker 622 may be saved as part of the navigation plan, and may include additional information relating to the biopsy, such as the date and time when the tissue sample was obtained, the results of related testing performed on the tissue sample, and/or other information related to the biopsy. The virtual marker 622 may also be used as a future target for planning additional pathways using the navigation plan. For example, application 81 may automatically create a pathway to stored virtual markers 622 based on the pathway planned for target 604 since the pathway is already known. Alternatively, the actual path taken to the virtual marker 622 by the LG 92 may be stored in association with the virtual marker 622. The clinician may also select which virtual markers 622 are displayed by activating a virtual marker menu 626 and selecting a virtual marker position 628 corresponding to the biopsy position number 620 from view 616, as shown, for example, in FIG. 5.

Figure 8:
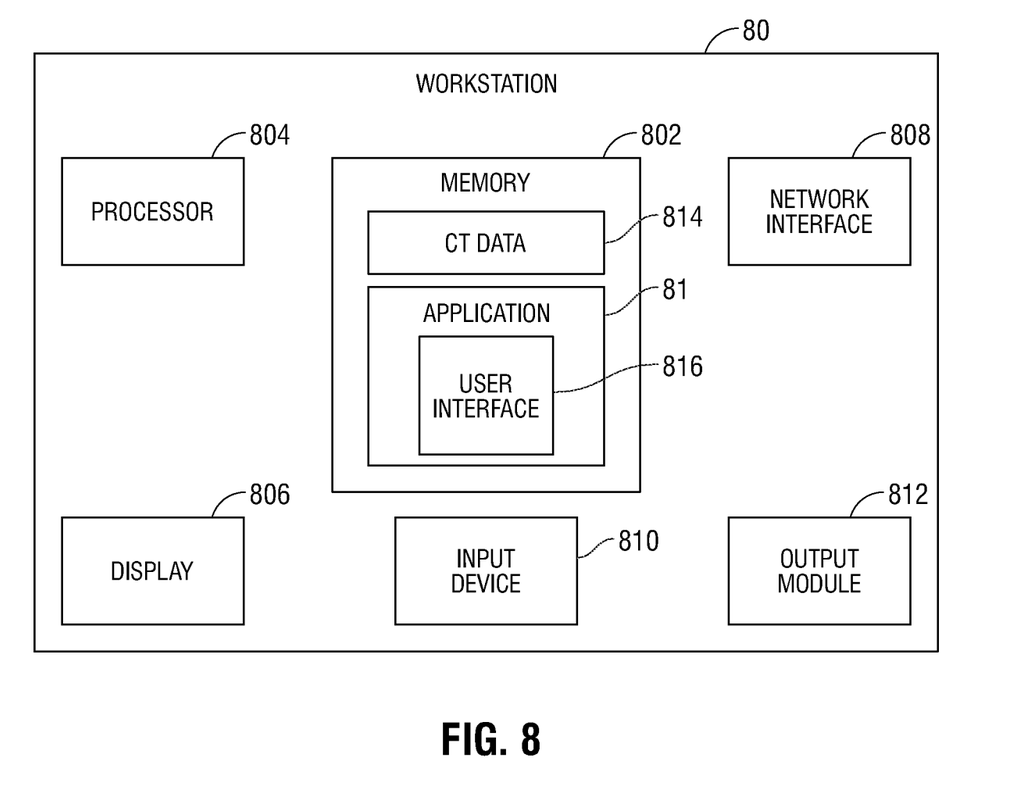
FIG. 8 is a schematic diagram of a workstation configured for use with the system of FIG. 3.

Turning now to FIG. 8, there is shown a system diagram of workstation 80. Workstation 80 may include memory 802, processor 804, display 806, network interface 208, input device 810, and/or output module 812.

Memory 802 includes any non-transitory computer-readable storage media for storing data and/or software that is executable by processor 804 and which controls the operation of workstation 80. In an embodiment, memory 802 may include one or more solid-state storage devices such as flash memory chips. Alternatively or in addition to the one or more solid-state storage devices, memory 802 may include one or more mass storage devices connected to the processor 804 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 804. That is, computer readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, Blu-Ray or other optical storage, magnetic cassettes, magnetic tape, magnetic disk storage or other magnetic storage devices, or any other medium which can be used to store the desired information and which can be accessed by workstation 80.

Memory 802 may store application 81 and/or CT data 814. Application 81 may, when executed by processor 804, cause display 806 to present user interface 816. Network interface 208 may be configured to connect to a network such as a local area network (LAN) consisting of a wired network and/or a wireless network, a wide area network (WAN), a wireless mobile network, a Bluetooth network, and/or the internet. Input device 810 may be any device by means of which a user may interact with workstation 80, such as, for example, a mouse, keyboard, foot pedal, touch screen, and/or voice interface. Output module 812 may include any connectivity port or bus, such as, for example, parallel ports, serial ports, universal serial busses (USB), or any other similar connectivity port known to those skilled in the art.

Various methods for generating the 3D model are envisioned, some of which are more fully described in co-pending U.S. Patent Publication Nos. 2014/0281961, 2014/0270441, and 2014/0282216, all entitled PATHWAY PLANNING SYSTEM AND METHOD, filed on Mar. 15, 2013, by Baker, the entire contents of all of which are incorporated herein by reference. A location sensor may be incorporated into different types of tools and catheters to track the location and assist in navigation of the tools. Navigation of the location sensor or tool is more fully described in co-pending U.S. patent application Ser. No. 14/753,288, entitled SYSTEM AND METHOD FOR NAVIGATING WITHIN THE LUNG, filed on Jun. 29, 2015, by Brown et al., the entire contents of which is incorporated herein by reference. The tracked location of the location sensor may also be used to virtually mark on a three-dimensional model of the airways of a patient the location within the airways of the patient where a biopsy or treatment is performed.

Additional features of the EMN system of the present disclosure are described in co-pending U.S. patent application Ser. No. 14/754,058, entitled INTELLIGENT DISPLAY, filed on Jun. 29, 2015, by KEHAT et al. Ser. No. 14/788,952, entitled UNIFIED COORDINATE SYSTEM FOR MULTIPLE CT SCANS OF PATIENT LUNGS, filed on Jul. 1, 2015, by Greenburg; Ser. No. 14/790,395, entitled ALIGNMENT CT, filed on Jul. 2, 2015, by Klein et al.; Ser. No. 14/725,300, entitled FLUOROSCOPIC POSE ESTIMATION, filed on May 29, 2015, by Merlet; Ser. No. 14/753,674, entitled TRACHEA MARKING, filed on Jun. 29, 2015, by Lachmanovich et al.; Ser. Nos. 14/755,708, and 14/755,721, both entitled SYSTEM AND METHOD FOR DETECTING TRACHEA, filed on Jun. 30, 2015, by Markov et al.; Ser. No. 14/754,867, entitled SYSTEM AND METHOD FOR SEGMENTATION OF LUNG, filed on Jun. 30, 2015, by Markov et al.; Ser. No. 14/790,107, entitled SYSTEM AND METHOD OF PROVIDING DISTANCE AND ORIENTATION FEEDBACK WHILE NAVIGATING IN 3D, filed on Jul. 2, 2015, by Lachmanovich et al.; and Ser. No. 14/751,257, entitled DYNAMIC 3D LUNG MAP VIEW FOR TOOL NAVIGATION INSIDE THE LUNG, filed on Jun. 26, 2015, by Weingarten et al., the entire contents of all of which are incorporated herein by reference.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting but merely as exemplifications of particular embodiments. Those skilled in the art will envision other modifications within the scope and spirit of the claims appended hereto.

What is claimed is:

1. A bronchial piercing catheter assembly used to pierce an airway wall of a patient and navigate to target tissue located outside the airway wall of the patient, the bronchial piercing catheter assembly comprising:
   an extended working channel defining a lumen;
   a bronchial piercing catheter configured to be positioned within the lumen of the extended working channel and movable relative to the extended working channel, the bronchial piercing catheter including:
      a shaft defining a central longitudinal axis and including a proximal end and a distal end; and
      a catheter tip located on the distal end of the shaft and configured to penetrate the airway wall, the catheter tip including:
         a base section defined along the central longitudinal axis;
         a trailing tip section distal to the base section, wherein the trailing tip section tapers relative to the base section; and
         a leading tip section distal to the trailing tip section, wherein the leading tip section further tapers to a distal point at an angle less than the trailing tip section when measured from a proximal direction along the central longitudinal axis.

2. The bronchial piercing catheter assembly of claim 1, wherein the catheter tip is titanium.

3. The bronchial piercing catheter assembly of claim 1, wherein sections of the catheter tip have a thickness ranging from about 0.06 inches to about 0.09 inches.

4. The bronchial piercing catheter assembly of claim 1, wherein the shaft includes an inner layer and an outer layer, wherein the inner layer is comprised of a composite.

5. The bronchial piercing catheter assembly of claim 4, wherein the inner layer has a thickness ranging from about 0.05 inches to about 0.07 inches.

6. The bronchial piercing catheter assembly of claim 4, wherein the composite is a braided polymer composite.

7. The bronchial piercing catheter assembly of claim 1, wherein at least one of the extended working channel or the bronchial piercing catheter includes a location sensor in operative communication with a navigation system configured to determine a location of at least one of the extended working channel or the bronchial piercing catheter.

8. The bronchial piercing catheter assembly of claim 1, wherein a length of the leading tip section is less than a length of the trailing tip section.

9. The bronchial piercing catheter assembly of claim 1, wherein the extended working channel is movable relative to the bronchial piercing catheter such that a distal end of the extended working channel is slideable over the shaft of the bronchial piercing catheter through the airway wall and proximate the target tissue.

10. A system for navigating a surgical instrument to target tissue located outside an airway of a patient, the system comprising:
a bronchial piercing catheter comprising:
a shaft defining a central longitudinal axis;
a catheter tip disposed at a distal end of the shaft and configured to puncture through an airway wall of the airway, the catheter tip including:
a base section defined along the central longitudinal axis;
a trailing tip section distal to the base section, wherein the trailing tip section tapers relative to the base section; and
a leading tip section distal to the trailing tip section, the leading tip section further tapering to a distal point at an angle less than the trailing tip section when measured from a proximal direction along the central longitudinal axis, wherein a length of the leading tip section is less than a length of the trailing tip section; and
a tracking system configured to track a position of the bronchial piercing catheter.

11. The system of claim 10, wherein the catheter tip is titanium.

12. The system of claim 10, wherein sections of the catheter tip have a thickness ranging from about 0.06 inches to about 0.09 inches.

13. The system of claim 10, wherein the bronchial piercing catheter includes a location sensor in operative communication with the tracking system.

14. The system of claim 13, wherein the location sensor is an electromagnetic sensor.

15. The system of claim 10, further comprising:
an extended working channel defining a lumen, wherein the bronchial piercing catheter is positionable within and removable from the lumen of the extended working channel; and
a surgical instrument positionable within the lumen of the extended working channel when the bronchial piercing catheter is removed from the lumen.

16. The system of claim 15, wherein the extended working channel includes a location sensor in operative communication with the tracking system and the tracking system is configured to track a position of the location sensor of the extended working channel.

17. The system of claim 15, wherein the surgical instrument is at least one of a biopsy tool or a microwave ablation device.

18. A system for navigating to target tissue located outside an airway of a patient, the system comprising:
a bronchial piercing catheter configured to be positioned within, and removed from, a lumen of an extended working channel and movable relative to the extended working channel, the bronchial piercing catheter including:
a shaft defining a central longitudinal axis and including a proximal end and a distal end; and
a catheter tip located on the distal end of the shaft and configured to penetrate an airway wall, the catheter tip including:
a base section defined along the central longitudinal axis;
a trailing tip section distal to the base section, wherein the trailing tip section tapers relative to the base section; and
a leading tip section distal to the trailing tip section, wherein the leading tip section further tapers to a distal point at an angle less than the trailing tip section when measured from a proximal direction along the central longitudinal axis; and
a surgical instrument configured to be positioned within, and removed from, the lumen of the extended working channel when the bronchial piercing catheter is removed from the lumen.

19. The system of claim 18, further comprising an extended working channel configured to slide over the bronchial piercing catheter after the catheter tip of the bronchial piercing catheter penetrates through the airway wall.

20. The system of claim 18, wherein the surgical instrument is at least one of a biopsy tool or a microwave ablation device.

* * * * *